(12) United States Patent
Sotoguchi et al.

(10) Patent No.: US 6,608,214 B2
(45) Date of Patent: Aug. 19, 2003

(54) PROCESS FOR PRODUCING OPTICALLY ACTIVE γ-BUTYROLACTONE

(75) Inventors: Tsukasa Sotoguchi, Hiratsuka (JP); Takaji Matsumoto, Hiratsuka (JP); Motonobu Takenaka, Hiratsuka (JP); Takashi Miura, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 10/199,136

(22) Filed: Jul. 19, 2002

(65) Prior Publication Data

US 2003/0105341 A1 Jun. 5, 2003

(30) Foreign Application Priority Data

Jul. 19, 2001 (JP) ........................................ 2001-220342

(51) Int. Cl.⁷ ............................................. C07D 307/33
(52) U.S. Cl. ....................................................... 549/313
(58) Field of Search .......................................... 549/313

(56) References Cited

FOREIGN PATENT DOCUMENTS

| EP | 0 583 171 A2 | 2/1994 |
| EP | 0 761 642 A2 | 3/1997 |
| EP | 0 761 663 A1 | 3/1997 |
| EP | 0 787 718 A1 | 8/1997 |
| EP | 1 176 135 A1 | 1/2002 |
| WO | WO 99/23086 | 4/1999 |
| WO | WO 00/05401 | 2/2000 |
| WO | WO 01/72681 A1 | 10/2001 |

OTHER PUBLICATIONS

A. Tanaka et al., *Synthesis*, pp. 570–573 (1987).
S. Saito, *Chemistry Letters*, pp. 1389–1392 (1984).
D. Seebach et al., *Synthesis*, pp. 37–40 (1986).
Patent Abstracts of Japan No. JP61–63690A., Apr. 1, 1986.
Patent Abstracts of Japan No. JP62–265293A, Nov. 18, 1987.
Patent Abstracts of Japan No. JP4–139140A, May 13, 1992.
Patent Abstracts of Japan No. JP10–182678A, Jul. 7, 1998.
Patent Abstracts of Japan No. JP11–269185A, Oct. 5, 1999.
Patent Abstracts of Japan No. JP2000–16997A, Jan. 18, 2000.
K. Mashima et al., *J. Chem. Soc., Chem. Commun.*, pp. 1208–1210 (1989).
S. Saito et al., *Chemistry Letters*, pp. 1389–1392 (1984).
M. Burk et al., *J. Am. Chem. Soc.*, 117:4423–4424 (1995).
J. Sakaki et al., *J. Chem. Soc., Chem. Commun.*, pp. 434–435 (1991).

*Primary Examiner*—Tacfiq Solola
(74) *Attorney, Agent, or Firm*—Peter F. Corless; Christine C. O'Day; Edwards & Angell, LLP

(57) ABSTRACT

This invention provides a novel process for producing optically active 3-hydroxy-γ-butyrolactone in a short step, which is superior economically and in efficiency and industrially suitable by using a starting material which is inexpensive and easily available and reagents easy to handle. This invention relates to a process for producing optically active 3-hydroxy-γ-butyrolactone represented by formula I:

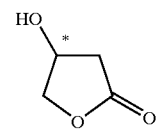

I wherein the symbol * means an asymmetric carbon atom, which comprises hydrogenating an optically active 4-substituted oxy-3-hydroxybutyrate represented by formula II:

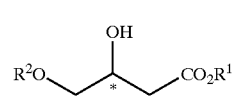

II wherein $R^1$ represents a $C_{1-4}$ lower alkyl group, $R^2$ represents a protective group for a hydroxyl group deprotected by hydrogenation with a heterogeneous hydrogenation catalyst, and the symbol * has the same meaning as defined above, in the presence of a heterogeneous hydrogenation catalyst and an acidic substance followed by deprotection and simultaneous ring closure thereof.

6 Claims, No Drawings

PROCESS FOR PRODUCING OPTICALLY ACTIVE γ-BUTYROLACTONE

BACKGROUND OF THE INVENTION

1. Field of the Invention

This invention relates to a novel production process capable of substantially producing optically active 3-hydroxy-γ-butyrolactone useful as a synthetic intermediate for pharmaceutical preparations and agrochemicals and as a functional material.

2. Description of the Related Art

The conventional process for producing optically active 3-hydroxy-γ-butyrolactone includes e.g. (1) a process for producing the same in 7 steps from D-isoascorbic acid and L-ascorbic acid as the starting materials (Synthesis, pp. 570–573, 1987), (2) a process for producing the same by reducing L-malic acid diester with a dimethyl sulfide/borane reagent and then subjecting the resultant diol ester to cyclization reaction with trifluoroacetic acid (Chemistry Letters, pp. 1389–1392, 1984), and (3) a process for producing the same by forming ethyl 4-tert-butoxy-3-hydroxybutyrate in 2 steps from ethyl 4-chloro-3-oxobutyrate and then cyclizing it in trifluoroacetic acid (Synthesis, pp. 37–40, 1986).

However, the process (1) is conducted through plural steps as many as 7 to make the procedure complicated, and this process is not desirable in respect of yield too. The process (2) has a problem that the dimethyl sulfide/borane reagent used in the production is expensive and difficult to handle. In the process (3), the product is produced in relatively short steps, but corrosive and toxic trifluoroacetic acid serving not only as a reagent but also as a solvent is used in a large amount, and low-temperature reaction is required, so this process cannot be said to be an industrial process.

Further, 3-hydroxy-γ-butyrolactone is water-soluble, and in any processes (1) to (3), washing with water is necessary at the stage of post-treatment after the reaction is finished, thus making the procedure troublesome and often lowering the yield, and therefore these cannot be said to be efficient processes.

Accordingly, it cannot be said from an economical viewpoint and in respect of efficiency that the prior art processes are industrially suitable production processes, and there is demand for development of an industrially suitable process for producing optically active 3-hydroxy-γ-butyrolactone.

SUMMARY OF THE INVENTION

The object of this invention is to provide a novel process for producing optically active 3-hydroxy-γ-butyrolactone in a short step, which is superior economically and in efficiency and industrially suitable by using a starting material which is inexpensive and easily available and reagents easy to handle.

Under these circumstances, the present inventors made an extensive study for solving the object described above. As a result, they found that an optically active 4-substituted oxy-3-hydroxybutyrate obtained by asymmetrically hydrogenating an easily available 4-substituted oxy-3-oxobutyrate is hydrogenated in the presence of a heterogeneous hydrogenation catalyst and an acidic substance followed by deprotection and simultaneous ring closure thereof, whereby optically active 3-hydroxy-γ-butyrolactone of high optical purity can be obtained in high yield, and this invention was thereby completed.

That is, this invention relates to a process for producing optically active 3-hydroxy-γ-butyrolactone represented by formula I:

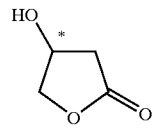

wherein the symbol * means an asymmetric carbon atom, which comprises hydrogenating an optically active 4-substituted oxy-3-hydroxybutyrate represented by formula II:

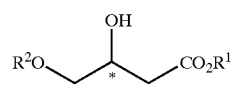

wherein $R^1$ represents a $C_{1-4}$ lower alkyl group, $R^2$ represents a protective group for a hydroxyl group deprotected by hydrogenation with a heterogeneous hydrogenation catalyst, and the symbol * has the same meaning as defined above, in the presence of a heterogeneous hydrogenation catalyst and an acidic substance followed by deprotection and simultaneous ring closure thereof.

Further, this invention relates to the process for producing optically active 3-hydroxy-γ-butyrolactone, wherein the optically active 4-substituted oxy-3-hydroxybutyrate represented by the general formula II above is obtained by asymmetrically hydrogenating a 4-substituted oxy-3-oxobutyrate represented by the general formula III:

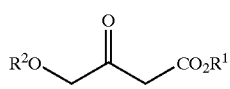

wherein $R^1$ and $R^2$ have the same meanings as defined above, in the presence of a ruthenium complex comprising an optically active phosphine compound as a ligand.

Further, this invention relates to the process for producing optically active 3-hydroxy-γ-butyrolactone, wherein R 2is an optionally substituted benzyl group, more preferably a benzyl group.

Further, this invention relates to the process for producing optically active 3-hydroxy-γ-butyrolactone, wherein the metal catalyst is a heterogeneous catalyst of palladium, iridium, rhodium, ruthenium, nickel, osmium or platinum.

Further, this invention relates to the process for producing optically active 3-hydroxy-γ-butyrolactone, wherein the acidic substance is p-toluenesulfonic acid, methanesulfonic acid, camphor sulfonic acid, sulfuric acid, trifluoroacetic acid, ferric chloride, zinc chloride or stannic chloride.

DETAILED DESCRIPTION OF THE INVENTION

Hereinafter, this reaction is described in more detail.

The process for producing optically active 3-hydroxy-γ-butyrolactone according to this invention is conducted according to the following reaction scheme:

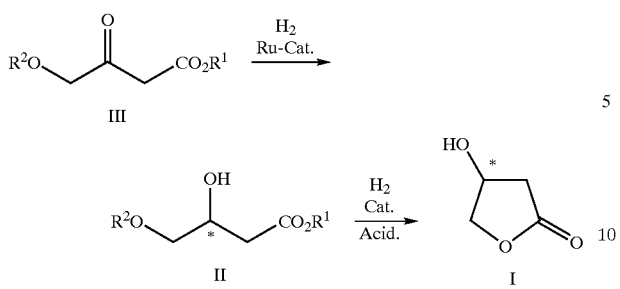

wherein $R^1$ represents a $C_{1-4}$ lower alkyl group, $R^2$ represents a protective group for a hydroxyl group deprotected by hydrogenation with a heterogeneous hydrogenation catalyst, and the symbol * means an asymmetric carbon atom.

That is, the optically active 4-substituted oxy-3-hydroxybutyrate (II) is hydrogenated in the presence of a heterogeneous hydrogenation catalyst and an acidic substance followed by deprotection and simultaneous ring closure thereof, whereby optically active 3-hydroxy-γ-butyrolactone (I) is formed. The optically active 4-substituted oxy-3-hydroxybutyrate (II) used as the starting material in this process can be produced by asymmetrically hydrogenating preferably a 4-substituted oxy-3-oxobutyrate (III) in the presence of a ruthenium complex comprising an optically active phosphine compound as a ligand.

The reaction scheme described above shows a series of these reactions.

In this invention, $R^1$ in the optically active 4-substituted oxy-3-hydroxybutyrate (II) may be a group capable of cleavage with its adjacent oxygen atom by participating in the reaction under the reaction conditions used, and the type of this group is not important, but the group is preferably a lower alkyl group such as methyl group, ethyl group, propyl group, isopropyl group, n-butyl group, isobutyl group, sec-butyl group or tert-butyl group, more preferably a $C_{1-4}$ lower alkyl group.

In this invention, $R^2$ in the optically active 4-substituted oxy-3-hydroxybutyrate (II) may be a hydroxyl-protecting group capable of cleavage upon deprotection under the reaction conditions for producing optically active 3-hydroxy-γ-butyrolactone (I), and the protective group for a hydroxyl group deprotected by hydrogenation with the heterogeneous hydrogenation catalyst is preferably a benzyl group which may have one or more substituent groups thereon. The substituent groups on the benzyl group are not particularly limited insofar as the benzyl group can act as a protective group capable of deprotection, and preferable examples thereof include a lower alkyl group such as methyl group and ethyl group, a lower alkoxy group such as methoxy group, an aryl group such as phenyl group, p-methoxyphenyl group and naphthyl group, a halogen atom such as fluorine atom and chlorine atom, and a nitro group. The benzyl group may be substituted with these substituent groups on either its phenyl ring or its methylene group.

Examples of $R^2$ include a benzyl group, p-methyl phenyl methyl group, p-ethyl phenyl methyl group, p-methoxy phenyl methyl group, 3,5-dimethyl phenyl methyl group, 3,5-dimethoxy phenyl methyl group, p-chlorophenyl methyl group, 2,6-dichlorophenyl methyl group, α-phenyl ethyl group, o-nitrophenyl methyl group, p-nitrophenyl methyl group, p-cyanophenyl methyl group, diphenyl methyl group, triphenyl methyl group, naphthyl methyl group, naphthyl diphenyl methyl group and p-methoxy phenyl diphenyl methyl group. More preferable examples of $R^2$ include a benzyl group, p-methyl phenyl methyl group, p-ethyl phenyl methyl group, p-methoxy phenyl methyl group, 3,5-dimethyl phenyl methyl group, 3,5-dimethoxy phenyl methyl group, p-fluorophenyl methyl group, p-chlorophenyl methyl group and α-phenyl ethyl group. $R^2$ is most preferably a benzyl group.

The optically active 4-substituted oxy-3-hydroxybutyrate (II) as the starting material in this invention is a known compound and can be produced by various methods, preferably by asymmetric hydrogenation of the 4-substituted oxy-3-oxobutyrate (III) in the presence of a ruthenium complex comprising an optically active phosphine compound as a ligand.

The substituent groups $R^1$ and $R^2$ on the 4-substituted oxy-3-oxobutyrate (III) are defined as being identical with, but may be different from, $R^1$ and $R^2$ on the compound represented by formula II above. $R^1$ and $R^2$ in formula II are groups to be eliminated under the reaction conditions, while $R^1$ and $R^2$ in formula III are groups acting as protective groups under the reaction conditions used. Accordingly, $R^1$ and $R^2$ in production of the starting material may be different from $R^1$ and $R^2$ in the conversion of the starting material into lactone, but the substituent groups $R^1$ and $R^2$ in the former step are preferably identical with $R^1$ and $R^2$ in the latter step in order to eliminate exchange the substituent groups with other ones.

Examples of the 4-substituted oxy-3-oxobutyrate (III) include methyl 4-benzyloxy-3-oxobutyrate, ethyl 4-benzyloxy-3-oxobutyrate, propyl 4-benzyloxy-3-oxobutyrate, isopropyl 4-benzyloxy-3-oxobutyrate, n-butyl 4-benzyloxy-3-oxobutyrate, tert-butyl 4-benzyloxy-3-oxobutyrate, methyl 4-(p-methylphenyl)methyloxy-3-oxobutyrate, ethyl 4-(p-methylphenyl)methyloxy-3-oxobutyrate, methyl 4-(p-ethylphenyl)methyloxy-3-oxobutyrate, ethyl 4-(p-ethylphenyl)methyloxy-3-oxobutyrate, methyl 4-(p-methoxyphenyl)methyloxy-3-oxobutyrate, ethyl 4-(p-methoxyphenyl)methyloxy-3-oxobutyrate, methyl 4-(α-phenylethyl)oxy-3-oxobutyrate, ethyl 4-(α-phenylethyl)oxy-3-oxobutyrate etc.

More preferably, methyl 4-benzyloxy-3-oxobutyrate and ethyl 4-benzyloxy-3-oxobutyrate can be mentioned.

In a preferable aspect of this invention, the 4-substituted oxy-3-oxobutyrate represented by the general formula III is asymmetrically hydrogenated in the presence of a ruthenium complex comprising an optically active phosphine compound as a ligand, whereby the optically active 4-substituted oxy-3-hydroxybutyrate (II) is produced.

The optically active phosphine compound used for asymmetrically hydrogenating the 4-substituted oxy-3-oxobutyrate used in this process is an optically active phosphine compound represented by the general formula IV:

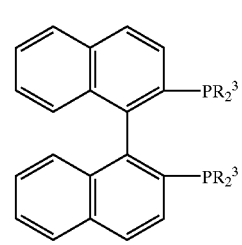

IV wherein $R^3$ represents an optionally substituted aryl group or a $C_{3-8}$ cycloalkyl group.

In the general formula IV, $R^3$ is preferably an optionally substituted phenyl group, an optionally substituted naphthyl group, or a $C_{3-8}$ cycloalkyl group.

The substituent group which may be present thereon includes e.g. a $C_{1-4}$ lower alkyl group such as methyl, ethyl, propyl, isopropyl, n-butyl, t-butyl and isobutyl; a halogen atom such as fluorine, chlorine and bromine; a $C_{1-4}$ lower alkoxy group such as methoxy, ethoxy, propoxy and butoxy; and a halogenated lower alkyl group such as trifluoromethyl and trichloromethyl, or an benzyloxy group.

Preferable examples of $R^3$ include a phenyl group, 4-tolyl group, 3-tolyl group, 4-methoxyphenyl group, 3,5-xylyl group, 3,5-di-tert-butyl phenyl group, 4-methoxy-3,5-dimethyl phenyl group, 4-methoxy-3,5-di-tert-butyl phenyl group, naphthyl group, cyclohexyl group and cyclopentyl group.

Preferably used optically active phosphine compounds of the general formula IV are for example tertiary phosphine compounds described in e.g. Japanese Patent Laid-Open Nos. 63690/1986 and 265293/1987, and specifically mention can be made of:

- 2,2'-bis(diphenylphosphino)-1,1'-binaphthyl (abbreviated hereinafter to "BINAP"),
- 2,2'-bis[di(p-tolyl)phosphino]-1,1'-binaphthyl (abbreviated hereinafter to "p-Tol-BINAP"),
- 2,2'-bis[di(3,5-xylyl)phosphino]-1,1'-binaphthyl (abbreviated hereinafter to "DM-BINAP"),
- 2,2'-bis[di(3,5-di-tert-butylphenyl)phosphino]-1,1'-binaphthyl (abbreviated hereinafter to "t-Bu-2-BINAP"),
- 2,2'-bis[di(4-methoxy-3,5-dimethylphenyl)phosphino]-1,1'-binaphthyl (abbreviated hereinafter to "DMM-BINAP"),
- 2,2'-bis(dicyclohexylphosphino)-1,1'-binaphthyl (abbreviated hereinafter to "Cy-BINAP"), and
- 2,2'-bis(dicyclopentylphosphino)-1,1'-binaphthyl (abbreviated hereinafter to "Cp-BINAP").

Other optically active phosphine compounds used in asymmetric hydrogenation include optically active phosphine compounds represented by the general formula V:

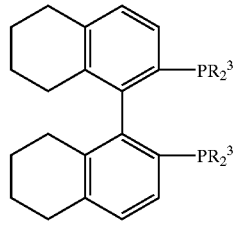

V wherein $R^3$ represents an optionally substituted aryl group or a $C_{3-8}$ cycloalkyl group.

$R^3$ in the general formula V includes the groups enumerated above.

Preferably used optically active phosphine compounds of the general formula V are for example tertiary phosphine compounds described in e.g. Japanese Patent Laid-Open No. 139140/1992, and specifically mention can be made of:

- 2,2'-bis{diphenylphosphino}-5,5',6,6',7,7',8,8'-octahydrobinaphthyl (abbreviated hereinafter to "H8-BINAP"),
- 2,2'-bis{di-p-tolylphosphino}-5,5',6,6',7,7',8,8'-octahydrobinaphthyl (abbreviated hereinafter to "p-Tol-H8-BINAP"),
- 2,2'-bis{di-(3,5-xylyl)phosphino}-5,5',6,6',7,7',8,8'-octahydrobinaphthyl (abbreviated hereinafter to "DM-H8-BINAP"), and
- 2,2'-bis{di-(4-methoxy-3,5-dimethylphenyl)phosphino}-5,5',6,6',7,7',8,8'-octahydrobinaphthyl (abbreviated hereinafter to "DMM-H8-BINAP").

Other optically active phosphine compounds used in asymmetric hydrogenation include optically active phosphine compounds represented by the general formula VI:

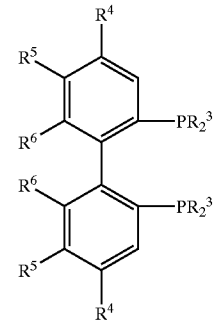

VI wherein $R^3$ represents an optionally substituted aryl group or a $C_{3-8}$ cycloalkyl group, $R^4$ represents a hydrogen atom or a $C_{1-4}$ lower alkyl group, $R^5$ represents a hydrogen atom, methyl group, methoxy group or halogen atom, and $R^6$ represents a methyl group or methoxy group, or $R^5$ and $R^6$ may be combined to form a methylene dioxy group.

$R^3$ in the general formula VI includes the groups enumerated above.

Preferably used optically active phosphine compounds of the general formula VI are for example optionally active tertiary phosphine compounds described in e.g. Japanese Patent Laid-Open Nos. 182678/1998, 269185/1999 and 16997/2000, and specifically mention can be made of:

- ((5,6),(5',6')-bis(methylenedioxy) biphenyl-2,2'-diyl)bis (diphenyl phosphine) (abbreviated hereinafter to "SEGPHOS"),
- ((5,6),(5',6')-bis(methylenedioxy) biphenyl-2,2'-diyl)bis (di-p-tolyl phosphine) (abbreviated hereinafter to "p-Tol-SEGPHOS"),
- ((5,6),(5',6')-bis(methylenedioxy) biphenyl-2,2'-diyl)bis (di-3,5-xylyl phosphine) (abbreviated hereinafter to "DM-SEGPHOS"),
- ((5,6),(5',6')-bis(methylenedioxy) biphenyl-2,2'-diyl)bis (di-4-methoxy-3,5-dimethylphenyl phosphine) (abbreviated hereinafter to "DMM-SEGPHOS"),
- ((5,6),(5',6')-bis(methylenedioxy) biphenyl-2,2'-diyl)bis (di-4-methoxy-3,5-di-tert-butylphenyl phosphine) (abbreviated hereinafter to "DTBM-SEGPHOS"), and
- ((5,6),(5',6')-bis(methylenedioxy) biphenyl-2,2'-diyl)bis (dicyclohexyl phosphine) (abbreviated hereinafter to "Cy-SEGPHOS").

Other compounds represented by the general formula VI include the following optically active phosphines:

- 2,2'-dimethyl-6,6'-bis(diphenyl phosphino)-1,1'-biphenyl (abbreviated hereinafter to "BIPHEMP"),
- 2,2'-dimethyl-6,6'-bis(di-p-tolyl phosphino)-1,1'-biphenyl (abbreviated hereinafter to "p-Tol-BIPHEMP"),
- 2,2'-dimethyl-6,6'-bis(di-3,5-xylyl phosphino)-1,1'-biphenyl (abbreviated hereinafter to "DM-BIPHEMP"),
- 2,2'-dimethyl-6,6'-bis(di-4-methoxy-3,5-dimethylphenyl phosphino)-1,1'-biphenyl (abbreviated hereinafter to "DMM-BIPHEMP"),
- 2,2'-dimethyl-6,6'-bis(di-4-t-butoxy-3,5-dimethylphenyl phosphino)-1,1'-biphenyl (abbreviated hereinafter to "DTBM-BIPHEMP"), 2,2'-dimethyl-6,6'-bis(dicyclohexyl phosphino)-1,1'-biphenyl (abbreviated hereinafter to "Cy-BIPHEMP"), 2,2'-dimethoxy-6,6'-bis(diphenyl phosphino)-1,1'-biphenyl (abbreviated hereinafter to "MeO-BIPHEP"), 2,2'-dimethoxy-6,6'-bis(di-p-tolyl phosphino)-1,1'-biphenyl (abbreviated hereinafter to "p-Tol-MeO-BIPHEP"), 2,2'-dimethoxy-6,6'-bis(di-3,5-xylyl phosphino)-1,1'-biphenyl (abbreviated hereinafter to "DM-MeO-BIPHEP"), 2,2'-dimethoxy-6,6'-bis(di-4-methoxy-3,5-dimethyl phenyl phosphino)-1,1'-biphenyl (abbreviated hereinafter to "DMM-MeO-BIPHEP"), 2,2'-dimethoxy-6,6'-bis(di-4-t-butoxy-3,5-dimethyl phenyl phosphino)-1,1'-biphenyl (abbreviated hereinafter to "DTBM-MeO-BIPHEP"), 2,2'-dimethoxy-6,6'-bis(dicyclohexyl phosphino)-1,1'-biphenyl (abbreviated hereinafter to "Cy-MeO-BIPHEP"), 2,2'-dimethyl-3,3'-dichloro-4,4'-dimethyl-6,6'-bis(di-p-tolyl phosphino)-1,1'-biphenyl (abbreviated hereinafter to "p-Tol-CM-BIPHEMP"), 2,2'-dimethyl-3,3'-dichloro-4,4'-dimethyl-6,6'-bis(di-3,5-xylyl phosphino)-1,1'-biphenyl (abbreviated hereinafter to "DM-CM-BIPHEMP"), and 2,2'-dimethyl-3,3'-dichloro-4,4'-dimethyl-6,6'-bis(di-4-methoxy-3,5-dimethyl phenyl phosphino)-1,1'-biphenyl (abbreviated hereinafter to "DMM-CM-BIPHEMP").

In the above-described process of this invention, the 4-benzyloxy-3-oxobutyrate (III) is hydrogenated by a complex comprising ruthenium and at least one member selected from the optically active phosphine compounds represented by the general formulae IV, V and VI.

Because these optically active phosphine compounds occur with (R)- and (S)-configurations, one configuration may be selected depending on the absolute configuration of the desired optically active 4-benzyloxy-3-hydroxybutyrate. That is, the optically active phosphine compound of (S)-configuration may be used to prepare the product of (3R)-configuration, while the optically active phosphine compound of (R)-configuration may be used to prepare the product of (3S)-configuration.

The ruthenium complex used in this hydrogenation reaction can be prepared by heating [Ru(p-cymene)X$_2$]$_2$ (X is a chlorine atom, bromine atom or iodine atom) and L (L is an optically active phosphine compound) in methylene chloride and ethanol under stirring in accordance with a method described in a literature (K. Mashima, K. Kusano, T. Ohta, R. Noyori, H. Takaya, J. Chem. Soc., Chem. Commun., 1208 (1989)). Examples of the ruthenium complex include:

[RuCl(benzene) (L)]Cl,
[RuBr(benzene) (L)]Br,
[RuI(benzene) (L)]I,
[RuCl(p-cymene)(L)]Cl,
[RuBr(p-cymene)(L)]Br,
[RuI(p-cymene)(L)]I,
[RuCl(mesitylene)(L)]Cl,
[RuBr(mesitylene)(L)]Br,
[RuI(mesitylene)(L)]I,
[RuCl(hexamethylbenzene)(L)]Cl,
[RuBr(hexamethylbenzene)(L)]Br,
[RuI(hexamethylbenzene)(L)]I,
[{RuCl(L)}$_2$($\mu$-Cl)$_3$][NR$_2$Me$_2$],
[{RuCl(L)}$_2$($\mu$-Cl)$_3$][NH$_2$Et$_2$],
[{RuCl(L)}$_2$($\mu$-Cl)$_3$][NH$_2$Pr$_2$], and
[{RuCl(L)}$_2$($\mu$-Cl)$_3$][NH$_2$i-Pr$_2$].

Preferable examples of the ruthenium complex comprising the optically active phosphine complex of this invention as a ligand include the following ruthenium complexes using ((5,6),(5',6')-bis(methylenedioxy) biphenyl-2,2'-diyl)bis (biphenyl phosphine) (abbreviated into SEGPHOSs) as the optically active phosphine compounds:

[RuCl(benzene)]{(R)- or (S)-SEGPHOSs}]Cl,
[RuBr(benzene)]{(R)- or (S)-SEGPHOSs}]Br,
[RuI(benzene)]{(R)- or (S)-SEGPHOSs}]I,
[RuCl(p-cymene)]{(R)- or (S)-SEGPHOSs}]Cl,
[RuBr(p-cymene)]{(R)- or (S)-SEGPHOSs}]Br,
[RuI(p-cymene)]{(R)- or (S)-SEGPHOSs}]I,
[RuCl(mesitylene)]{(R)- or (S)-SEGPHOSs}]Cl,
[RuBr(mesitylene)]{(R)- or (S)-SEGPHOSs}]Br,
[RuI(mesitylene)]{(R)- or (S)-SEGPHOSs}]I,
[RuCl(hexamethylbenzene)]{(R)- or (S)-SEGPHOSs}]Cl,
[RuBr(hexamethylbenzene)]{(R)- or (S)-SEGPHOSs}]Br,
[RuI(hexamethylbenzene)]{(R)- or (S)-SEGPHOSs}]I,
[{RuCl {(R)- or (S)-SEGPHOSs}}$_2$($\mu$-Cl)$_3$][NH$_2$Me$_2$],
[{RuCl {(R)- or (S)-SEGPHOSs}}$_2$($\mu$-Cl)$_3$][NH$_2$Et$_2$],
[{RuCl {(R)- or (S)-SEGPHOSs}}$_2$($\mu$-Cl)$_3$][NH$_2$Pr$_2$], and
[{RuCl {(R)- or (S)-SEGPHOSs}}$_2$($\mu$-Cl)$_3$][NH$_2$i-Pr$_2$].

The asymmetric hydrogenation in this invention can be carried out by subjecting the 4-benzyloxy-3-oxobutyrate represented by the general formula III to asymmetric hydrogenation reaction in the presence of the ruthenium complex comprising an optically active phosphine compound as a ligand.

This reaction can be carried out in an organic solvent. The organic solvent includes e.g. aromatic hydrocarbons such as toluene, benzene and chlorobenzene, aliphatic esters such as ethyl acetate, propyl acetate and butyl acetate, ethers such as diethyl ether, diisopropyl ether and tetrahydrofuran, halogenated hydrocarbons such as dichloromethane and dichloroethane, and alcohols such as methanol, ethanol and isopropanol. These can be used alone or as a mixture of two or more solvents. The solvent is preferably an alcohol, more preferably methanol or ethanol.

The ratio by volume of the solvent to the starting compound (substrate) is in the range of about 0.1 to 10, preferably about 0.5 to 3.

The ruthenium complex used in the asymmetric hydrogenation reaction in this invention is used in an amount of about 1/20000 to 1/10 mole, preferably about 1/10000 to 1/100 mole, per mole of the starting compound (substrate).

The hydrogen pressure is in the range of about 0.5 to 10 MPa, preferably about 1 to 5 MPa.

The reaction temperature used is in the range of about 30 to 100° C., preferably about 60 to 90° C., and while the temperature is kept in this range, the reaction is carried out for about 1 to 100 hours, preferably 1 to 24 hours, whereby the asymmetric hydrogenation reaction can proceed smoothly.

The reaction solution obtained in the above reaction can be purified by known techniques such as solvent extraction, transfer to another solvent, distillation, crystallization, re-crystallization and chromatography to give the compound (II).

In the process of this invention, the optically active 4-substituted oxy-3-hydroxybutyrate represented by the general formula II, preferably the optically active 4-substituted oxy-3-hydroxybutyrate represented by the general formula II obtained by the method described above, is hydrogenated in the presence of a heterogeneous hydrogenation catalyst and an acidic substance followed by deprotection and simultaneous ring closure thereof to produce optically active 3-hydroxy-γ-butyrolactone (I).

As the heterogeneous hydrogenation catalyst used in the hydrogenation of the optically active 4-substituted oxy-3-hydroxybutyrate used in this invention, a conventionally used heterogeneous hydrogenation catalyst is used.

The heterogeneous hydrogenation catalyst includes e.g. Raney nickel, platinum oxide, platinum black, palladium black, rhodium black, palladium carbon, iridium carbon, rhodium carbon, ruthenium carbon, osmium carbon, palladium alumina, palladium silica and palladium silica alumina. The catalyst is preferably Raney nickel, platinum black, palladium black, palladium carbon, palladium alumina, palladium silica or palladium silica alumina. Among these, Raney nickel, palladium black and palladium carbon are more preferable because of high selectivity and yield in the reaction and usability for various purposes.

As the acidic substance used in the process of this invention, various acidic substances such as Lewis acid can be used. Examples of such acidic substances include sulfonic acids such as benzenesulfonic acid, p-toluenesulfonic acid, methanesulfonic acid, camphor sulfonic acid and sulfuric acid; perhalogenoacetic acids such as trifluoroacetic acid and trichloroacetic acid, and Lewis acids such as ferric chloride, zinc chloride and stannic chloride. Preferable acidic substances include e.g. p-toluenesulfonic acid, methanesulfonic acid and camphor sulfonic acid. Among these, p-toluenesulfonic acid and methanesulfonic acid are more preferable because of usability for various purposes and high selectivity and yield in the reaction. These acidic substances can be used singly or in combination thereof, but is used preferably singly.

This reaction can be carried out in an organic solvent. The organic solvent includes e.g. aromatic hydrocarbons such as toluene, benzene and chlorobenzene, aliphatic esters such as ethyl acetate, propyl acetate and butyl acetate, ethers such as diethyl ether, diisopropyl ether and tetrahydrofuran, halogenated hydrocarbons such as dichloromethane and dichloroethane, and alcohols such as methanol, ethanol and isopropanol. These can be used singly or as a mixture of two or more solvents. The solvent is preferably an alcohol, particularly methanol, ethanol, isopropanol and toluene. Among these alcohols, methanol, ethanol and isopropanol are more preferable because of usability for various purposes and high selectivity and yield in the reaction.

The amount of the solvent is not particularly limited, but the ratio by volume of the solvent to the starting compound (substrate) is in the range of about 0.1 to 10, preferably about 0.5 to 3.

The heterogeneous hydrogenation catalyst in this invention is used in the range of preferably about 0.02 to 20% by weight, more preferably about 0.1 to 5% by weight, relative to 1% by weight of the starting compound (substrate), but this range is not restrictive.

The acidic substance in this reaction is used in the range of preferably about 0.1 to 10% by weight, more preferably about 0.5 to 5% by weight, relative to 1% by weight of the starting compound (substrate), but this range is not restrictive.

The hydrogen pressure is preferably in the range of about 0.05 to 10 MPa, more preferably about 0.1 to 3 MPa, but this range is not restrictive.

The reaction temperature used is in the range of about 20 to 100° C., preferably about 30 to 60° C., and while the temperature is kept in this range, the reaction is carried out for about 1 to 50 hours, preferably 1 to 10 hours, whereby the hydrogenation reaction can proceed smoothly.

After the reaction is finished, the heterogeneous hydrogenation catalyst is removed by filtration from the reaction solution obtained in the above reaction, and the solvent is distilled away under reduced pressure. The resultant residues are distilled under reduced pressure, whereby optically active 3-hydroxy-γ-butyrolactone as the desired compound of this invention can be obtained with high purity and in high yield.

That is, the process of this invention is an efficient process because the process neither requires conventional techniques such as solvent extraction and transfer to another solvent, nor requires treatment in an aqueous solution in the reaction system or in post-treatment steps (isolation, purification etc.) to isolate and purify 3-hydroxy-γ-butyrolactone, thus eliminating necessity for extraction from the aqueous system to make the procedure simple and eliminate a loss in the aqueous system.

EXAMPLES

Hereinafter, this invention is described in more detail by reference to the Examples and the Comparative Examples, which are not intended to limit this invention and can be modified within the scope of this invention.

The measuring devices used in measurement of products in the Examples are as follows.

Gas chromatography (GLC): Model 5890-II (Hewlett-Packard Company)

Column: Silicon NB-1 (0.25 mm×30 m) (GL Sciences Inc.)

Injection temperature: 220° C.

Column temperature: Rising temperature at a rate of 5° C./min. from 100° C. to 250° C.

Detection temperature: 250° C.

High performance liquid chromatography (HPLC): Hitachi L-600 (Hitachi, Ltd.)

Column: CHIRALPAK AD-RH (0.46 cm×15 cm) (Daicel Chemical Industries, Ltd.)

Eluent: acetonitrile/water=35/65

Flow rate: 0.5 ml/min.

Detection: UV 220 nm

Optical rotation: Model DIP-360 (JASCO Corporation)

Example 1

Production of Ethyl (S)-4-Benzyloxy-3-hydroxybutyrate 300.0 g (1.27 moles) ethyl 4-benzyloxy-3-oxobutyrate, 300 ml ethanol, and 104.5 mg (0.127 mmol) [RuCl{(R)-segphos}]$_2$($\mu$-Cl)$_3$ [Me$_2$NH$_2$] were introduced in a nitrogen stream into a 1-L autoclave and flushed with hydrogen, and after introduction of hydrogen at a pressure of 1 MPa, the mixture was heated with stirring. The mixture was reacted at 90 to 95° C. for 7 hours. After the reaction solution was cooled to room temperature, the hydrogen was purged and replaced by nitrogen. The reaction solution was concentrated in a rotary evaporator and the residue was distilled under reduced pressure to give 263.3 g of the title compound (chemical purity, 96.2%; optical purity, 99.1% ee; and yield, 87%).

The physical properties of the resultant compound are as follows:

Boiling point: 124° C./0.3 mmHg;
Optical rotation: $[\alpha]_D^{24}$=−11.59°(c=1.50, CHCl$_3$)

Example 2

Production of (S)-3-Hydroxy-γ-butyrolactone 100.0 g (0.42 mole) ethyl (S)-4-benzyloxy-3-hydroxybutyrate, 100 ml isopropanol, 1.0 g p-toluenesulfonic acid and 2.0 g of 5% palladium carbon were introduced in a nitrogen stream into a 500-ml autoclave and flushed with hydrogen, and after introduction of hydrogen at a pressure of 2 MPa, the mixture was heated with stirring. The mixture was reacted at 60° C. for 1 hour. After the reaction solution was cooled to room temperature, the hydrogen was purged and replaced by nitrogen. After the catalyst was filtered off, the filtrate was concentrated in a rotary evaporator and the residue was distilled under reduced pressure to give 38.05 g of the title compound (chemical purity, 99.2%; yield, 88.8%).

The physical properties of the resultant compound are as follows:

Boiling point: 140° C./1 mmHg;
Optical rotation: $[\alpha]_D^{24}$=−85.04° (c=2.10, EtOH)

Example 3

Production of Ethyl (R)-4-Benzyloxy-3-hydroxybutyrate 300.0 g (1.27 moles) ethyl 4-benzyloxy-3-oxobutyrate, 300 ml ethanol, and 104.5 mg (0.127 mmol) [RuCl{(S)-segphos}]$_2$($\mu$-Cl)$_3$[Me$_2$NH$_2$] were introduced in a nitrogen stream into a 1-L autoclave and flushed with hydrogen, and after introduction of hydrogen at a pressure of 1 MPa, the mixture was heated with stirring. The mixture was reacted at 90 to 95° C. for 7 hours. After the reaction solution was cooled to room temperature, the hydrogen was purged and replaced by nitrogen. The reaction solution was concentrated in a rotary evaporator and the residue was distilled under reduced pressure to give 265.1 g of the title compound (chemical purity, 95.5%; optical purity, 99.1% ee; and yield, 87.6%).

The physical properties of the resultant compound are as follows:

Boiling point: 124° C./0.3 mmHg;
Optical rotation: $[\alpha]_D^{24}$=+11.25° (c=1.60, CHCl$_3$).

Example 4

Production of (R)-3-Hydroxy-γ-butyrolactone 100.0 g (0.42 mole) ethyl (R)-4-benzyloxy-3-hydroxybutyrate, 100 ml isopropanol, 1.0 g p-toluenesulfonic acid and 2.0 g of 5% palladium carbon were introduced in a nitrogen stream into a 500-ml autoclave and flushed with hydrogen, and after introduction of hydrogen at a pressure of 2 MPa, the mixture was heated with stirring. The mixture was reacted at 60° C. for 1 hour. After the reaction solution was cooled to room temperature, the hydrogen was purged and replaced by nitrogen. After the catalyst was filtered off, the filtrate was concentrated in a rotary evaporator and the residue was distilled under reduced pressure to give 37.20 g of the title compound (chemical purity, 99.0%; yield, 86.8%).

The physical properties of the resultant compound are as follows:

Boiling point: 140° C./1 mmHg;
Optical rotation: $[\alpha]_D^{24}$=+83.55° (c=2.00, EtOH)

Examples 5 to 17

Production of (R)-3-Hydroxy-γ-butyrolactone

In Examples 5 to 17, the same procedure as in Example 2 was carried except that the solvent, the amount thereof, the catalyst, the amount thereof, the acidic substance, the amount thereof, the hydrogen pressure, the reaction temperature and the reaction time used are those shown in Table 1. The results are shown in Table 1.

TABLE 1

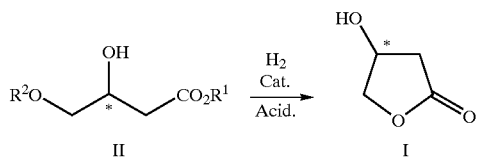

| Example | Solvent (S/S) | Catalyst (Wt %) | Acidic substance (Wt %) | H$_2$ MP$_a$ | Temperature (° C.) | Time (hr) | Yield (%) | Purity (%) |
|---|---|---|---|---|---|---|---|---|
| 5 | AcOEt (3) | 5% Pd—C (1) | PTSA (2) | 3 | 60 | 16 | 64 | 59 |
| 6 | EtOH (3) | 5% Pd—C (2.5) | PTSA (1) | 3 | 60 | 18 | 97 | 99 |
| 7 | IPA (1) | 5% Pd—C (2) | PTSA (1) | 3 | 60 | 16 | >99 | 97 |
| 8 | IPA (1) | 5% Pd—C (2) | PTSA (1) | 2 | 60 | 1 | 89 | >99 |
| 9 | IPA (1) | 5% Pd—C (2) | PTSA (1) | 2 | 30 | 2 | 97 | 96 |
| 10 | IPA (1) | 5% Pd—C (2) | H$_2$SO$_4$ (4) | 2 | 60 | 2 | 92 | 90 |
| 11 | IPA (1) | 5% Pd—C (2) | TFA (1) | 2 | 60 | 2 | 83 | 78 |

TABLE 1-continued $$R^2O\underset{*}{\overset{OH}{\diagdown}}CO_2R^1 \xrightarrow[\text{Acid.}]{\substack{H_2 \\ \text{Cat.}}} \underset{I}{\overset{HO}{\diagdown}}\underset{O}{\overset{*}{\diagdown}}$$

II                                I

| Example | Solvent (S/S) | Catalyst (Wt %) | Acidic substance (Wt %) | $H_2$ $MP_a$ | Temperature (° C.) | Time (hr) | Yield (%) | Purity (%) |
|---|---|---|---|---|---|---|---|---|
| 12 | IPA (1) | 5% Pd—C (2) | FeCl₃ (1) | 2 | 60 | 2 | 60 | 52 |
| 13 | IPA (1) | 5% Pd—C (0.5) | PTSA (1) | 2 | 60 | 2 | >99 | 97 |
| 14 | IPA (1) | 5% Pd—C (0.5) | PTSA (0.5) | 2 | 60 | 2 | >99 | 98 |
| 15 | IPA (1) | 5% Pd—C (0.5) | PTSA (0.5) | 0.5 | 60 | 2 | 98 | 98 |
| 16 | IPA (1) | 5% Pd—C (0.2) | PTSA (0.5) | 2 | 60 | 2 | >99 | 97 |
| 17 | IPA (1) | 5% Pd—C (0.1) | PTSA (0.5) | 2 | 60 | 6 | >99 | 97 |

In Table 1, IPA is isopropanol, PTSA is p-toluenesulfonic acid, and TFA is trifluoroacetic acid.

Comparative Example 1

100.0 g (0.42 mole) ethyl (S)-4-benzyloxy-3-hydroxybutyrate, 100 ml isopropanol and 2.0 g of 5% palladium carbon were introduced in a nitrogen stream into a 500-ml autoclave and flushed with hydrogen, and after introduction of hydrogen at a pressure of 2 MPa, the mixture was heated with stirring. The mixture was reacted at 60° C. for 1 hour. After the reaction solution was cooled to room temperature, the hydrogen was purged and replaced by nitrogen. After the catalyst was filtered off, the filtrate was concentrated in a rotary evaporator. Analysis of the residue indicated that the cyclized product could not be obtained, and the product was ethyl 3,4-dihydroxybutyrate.

Comparative Example 2

100.0 g (0.42 mole) ethyl (S)-4-benzyloxy-3-hydroxybutyrate, 100 ml isopropanol and 1.0 g p-toluenesulfonic acid were introduced in a nitrogen stream into a 500-ml autoclave and flushed with hydrogen, and after introduction of hydrogen at a pressure of 2 MPa, the mixture was heated with stirring. The mixture was reacted at 60° C. for 1 hour. After the reaction solution was cooled to room temperature, the hydrogen was purged and replaced by nitrogen. After the catalyst was filtered off, the filtrate was concentrated in a rotary evaporator. Analysis of the residue indicated that the reaction did not proceed, and the starting material ethyl (S)-4-benzyloxy-3-hydroxybutyrate was recovered.

As is evident from Table 1, Examples 2 and 4 and Comparative Examples 1 to 2, it was found when the reaction is carried out using the heterogeneous hydrogenation catalyst and the acidic substance, the desired cyclized product of good purity as high as 52% or more can be obtained in good yield as high as 60% or more.

However, when the reaction was carried out using the heterogeneous hydrogenation catalyst only in Comparative Example 1, the desired cyclized product could not be obtained, and the product was ethyl 3,4-dihydroxybutyrate.

Alternatively, when the reaction was carried out using the acidic catalyst only, the reaction did not proceed, and the starting material was merely recovered.

As described above, use of both the heterogeneous hydrogenation catalyst and the acidic substance in the reaction in this invention is very useful for completing this invention.

Industrial Applicability

According to the production process of this invention, optically active 3-hydroxy-γ-butyrolactone of high purity can be produced in high yield in one step from an optically active 4-substituted oxy-3-hydroxybutyrate obtained by asymmetric hydrogenation of an industrially easily available 4-substituted oxy-3-oxobutyrate.

The production process of this invention, as compared with the conventional processes, is an economically superior and industrially advantageous process without using a complicated synthetic route.

What is claimed is:

1. A process for producing optically active 3-hydroxy-γ-butyrolactone represented by formula I:

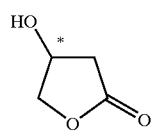

I wherein the symbol * means an asymmetric carbon atom, which comprises hydrogenating an optically active 4-substituted oxy-3-hydroxybutyrate represented by formula II:

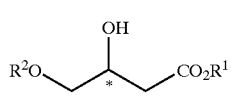

II wherein $R^1$ represents a $C_{1-4}$ lower alkyl group, $R^2$ represents a protective group for a hydroxyl group deprotected by hydrogenation with a heterogeneous hydrogenation catalyst, and the symbol * has the same meaning as defined above, in the presence of a heterogeneous hydrogenation catalyst and an acidic substance followed by deprotection and simultaneous ring closure thereof.

2. The process for producing optically active 3-hydroxy-γ-butyrolactone according to claim 1, wherein the 4-substituted oxy-3-hydroxybutyrate represented by formula II is obtained by asymmetrically hydrogenating a 4-substituted oxy-3-oxobutyrate represented by the general formula III:

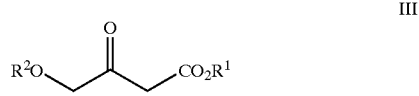

III wherein $R^1$ and $R^2$ have the same meanings as defined above, in the presence of a ruthenium complex comprising an optically active phosphine compound as a ligand.

3. The process for producing optically active 3-hydroxy-γ-butyrolactone according to claim 1 or 2, wherein $R^2$ is an optionally substituted benzyl group.

4. The process for producing optically active 3-hydroxy-γ-butyrolactone according to any one of claims 1 to 3, wherein $R^2$ is a benzyl group.

5. The process for producing optically active 3-hydroxy-γ-butyrolactone according to any one of claims 1 to 4, wherein the metal catalyst is a heterogeneous catalyst of palladium, iridium, rhodium, ruthenium, nickel, osmium or platinum.

6. The process for producing optically active 3-hydroxy-γ-butyrolactone according to any one of claims 1 to 5, wherein the acidic substance is p-toluenesulfonic acid, methanesulfonic acid, camphor sulfonic acid, sulfuric acid, trifluoroacetic acid, ferric chloride, zinc chloride, stannic chloride.

* * * * *